United States Patent [19]

Magarian et al.

[11] Patent Number: 4,879,315

[45] Date of Patent: Nov. 7, 1989

[54] CYCLOPROPYL ANALOGS AS ANTI-ESTROGENIC, ANTI-TUMOR AND FEMALE FERTILITY AGENTS

[75] Inventors: Robert A. Magarian; Joseph T. Pento, both of Norman, Okla.

[73] Assignee: The Board of Regents for the University of Oklahoma, Norman, Okla.

[21] Appl. No.: 98,945

[22] Filed: Sep. 21, 1987

Related U.S. Application Data

[63] Continuation-in-part of Ser. No. 363,429, Mar. 30, 1982, abandoned, which is a continuation-in-part of Ser. No. 166,255, Jul. 7, 1980, abandoned, which is a continuation-in-part of Ser. No. 128,040, Mar. 7, 1980, abandoned.

[51] Int. Cl.$^4$ ............................................. A61K 31/03
[52] U.S. Cl. ................................... 514/754; 424/422; 424/430; 424/433
[58] Field of Search ................ 514/754; 424/422, 430, 424/433

[56] References Cited

PUBLICATIONS

Margarian and Benjamin, "Synthesis of Cyclopropyl Analogs of Stilbene and Stilbenediol as Possible Antiestrogens", J. Pham. Sci., 64, 1626–32 (1975).

Primary Examiner—William R. Dixon, Jr.
Assistant Examiner—Jerry D. Johnson
Attorney, Agent, or Firm—Dunlap, Codding, Peterson & Lee

[57] ABSTRACT

Anti-estrogenic cyclopropyl analogs such as 1,1-dichlorocis-2,3-diphenylcyclopropane, when administered to a subject function as anti-tumor agents to prevent the development of estrogen-dependent tumors in the subject and substantially arrest the growth and metastatic involvement of existing estrogen-dependent tumors in the subject. Further, the anti-estrogenic cyclopropyl analogs may be used as anti-estrogenic agents and as fertility agents in the treatment of female infertility. The cyclopropyl analogs useful as anti-tumor, anti-estrogenic and female fertility agents have the general structure

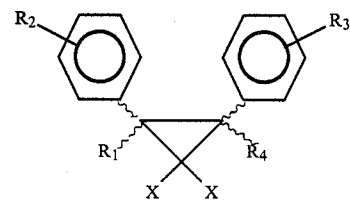

wherein:
X is a halogen or hydrogen atom;
$R_1$ is a hydrogen atom, an alkyl group containing from 1 to about 3 carbon atoms, a monocyclic group, a hydroxy substituted monocyclic group, an alkoxy substituted monocyclic group in which the alkyl substituent contains from 1 to about 3 carbon atoms or an acetoxy substituted monocyclic group;
$R_2$ is a hydrogen atom, an acetate group, a hydroxyl group, an alkoxy group in which the alkyl substituent contains from 1 to about 3 carbon atoms, a beta-dialkylaminoethoxy group wherein the alkyl substituent contains from 1 to about 6 carbon atoms, a beta-monoaminoheterocycloethoxy group, or pharmaceutically acceptable salts thereof;
$R_3$ is a hydrogen atom, an acetate group, a hydroxyl group, or an alkoxy group in which the alkyl substituent contains from 1 to about 3 carbon atoms;
$R_4$ is a hydrogen atom, or an alkyl group containing from 1 to about 3 carbon atoms; and
the wavy lines ( ) in the structure indicate that the anti-tumor agent can be the cis- or trans-isomers.

2 Claims, 2 Drawing Sheets

CYCLOPROPYL ANALOGS AS ANTI-ESTROGENIC, ANTI-TUMOR AND FEMALE FERTILITY AGENTS

CROSS-REFERENCE TO RELATED APPLICATIONS

This application is a continuation in part of U.S. patent application Ser. No. 363,429, filed Mar. 30, 1982 now abandoned, which is a continuation in part of U.S. patent application Ser. No. 166,255 now abandoned, filed July 7, 1980, which is a continuation in part of U.S. patent application Ser. No. 128,040, filed Mar. 7, 1980. These applications are incorporated herein by reference.

FIELD OF THE INVENTION

This invention relates to anti-estrogenic agents and their use in mammals for preventing or retarding development and growth of tumors, and more particularly, but not by way of limitation, to the use of cyclopropyl analogs as anti-estrogenic agents and as anti-tumor agents for preventing or retarding the development or growth of estrogen-dependent tumors.

In another aspect the present invention relates to the use of anti-estrogenic cyclopropyl analogs for the treatment of female infertility in a mammal.

DESCRIPTION OF THE PRIOR ART

Gem-dichlorocyclopropyl analogs, such as 1,1-dichloro-cis-2,3-diphenylcyclopropane, have heretofore been known. Such cyclopropyl analogs have been prepared using two different synthetic methods, namely, a two-phase catalytic method and an organo-mercurial method. Such gem-dichloro-cyclopropyl analogs have also been reduced to their corresponding cyclopropyl analogs via sodium and wet methanol.

Anti-estrogenic agents have heretofore been employed in the treatment of tumors, such as the estrogen-dependent tumors which normally occur in the breast and uterus of female subjects. These anti-tumor agents, while meeting with some success, have suffered in that such agents generally exhibit both estrogenic and anti-estrogenic properties. The combination of the estrogenic and anti-estrogenic properties often results in the failure of the agent to achieve complete regression of estrogen-dependent tumors because the estrogenic properties of such agents tend to promote the growth of the estrogen-dependent tumor while the anti-estrogenic properties of the agents attempt to retard or arrest the growth of the estrogen-dependent tumor. Thus, a need has long been recognized for new and improved anti-estrogenic agents which can be employed in the treatment of estrogen-dependent tumors and which do not possess undesired estrogenic activity.

SUMMARY OF THE INVENTION

According to the present invention we have discovered that cyclopropyl analogs of stilbene derivatives can be used to induce anti-estrogenic activity in a subject, can be used to prevent the development of estrogen-dependent tumors in a subject, or can be used to substantially arrest the growth and metastatic involvement of such tumors in the subject. The anti-estrogenic cyclopropyl analogs which can be administered in nontoxic dosages to subjects in need of anti-estrogenic activity, or having estrogen-dependent tumors or who are likely to develop such tumors are represented by the general structure wherein:
X is a halogen or hydrogen atom;
R₁ is a hydrogen atom, an alkyl group containing from 1 to about 3 carbon atoms, a monocyclic group, a hydroxy substituted monocyclic group, or an alkoxy substituted monocyclic group in which the alkyl substituent contains from 1 to about 3 carbon atoms;
R₂ is a hydrogen atom, an acetate group, a hydroxyl group, an alkoxy group in which the alkyl substituent contains from 1 to about 3 carbon atoms, a beta-dialkylaminoethoxy group in which the alkyl substituent contains from 1 to about 3 carbon atoms, a beta-monoaminoheterocycloethoxy group; or pharmaceuticalyy acceptable salts thereof;
R₃ is a hydrogen atom, an acetate group, a hydroxyl group, or an alkoxy group in which the alkyl substituent contains from 1 to about 3 carbon atoms;
R₄ is a hydrogen atom, or an alkyl group containing from 1 to about 3 carbon atoms; and
the wavy lines ($\sim$) in the structure indicate that the anti-tumor agent can be the cis- or trans-isomer.

Further, according to the present invention, the before described anti-estrogenic cyclopropyl analogs may be utilized as fertility agents in the treatment of an infertile female subject.

Therefore, an object of the present invention is to provide an anti-estrogenic agent which can be administered to a subject. Another object is to provide an improved anti-tumor agent which can readily be administered to a subject and which can substantially prevent formation of estrogen-dependent tumors in the subject.

Another object of the present invention is to provide an improved anti-tumor agent which can be administered to a subject having an estrogen-dependent tumor to arrest the growth and development of the tumor while preventing metastatic involvement of such a tumor in the subject.

Another object of the present invention is to provide improved anti-tumor agents which do not possess estrogenic properties.

These and other objects, advantages and features of the present invention will be apparent to those skilled in the art from a reading of the following detailed description when read in conjunction with the drawings which accompany this disclosure and with the appended claims.

DETAILED DESCRIPTION OF PREFERRED EMBODIMENTS

As previously stated, the present invention relates to cyclopropyl analogs and their use as anti-tumor agents in the prevention and/or treatment of estrogen-dependent tumors. In addition, such cyclopropyl analogs may find additional use as fertility agents in the treatment of an infertile female subject.

In order to assist in the understanding of the subject invention, as well as the terminology used herein, the following definitions are set forth.

The term "anti-estrogenic" as used herein is to be understood to refer to those substances which bind to the estrogen receptor and impede the estrogenic response of estradiol without producing an estrogenic effect. This category of antiestrogen is referred to as "pure" anti-estrogens. However, an anti-estrogenic compound may also bind to the estrogen receptor producing an estrogenic response while at the same time impeding the estrogenic activity of estradiol.

"Dosage" is the amount of the cyclopropyl analog administered to a subject during a twenty-four (24) hour period to produce the desired therapeutic effect within the subject.

The term "subject" as used herein is to be understood to mean mammals, including humans, household animals, such as dogs and cats, and large animals such as horses, cattle and the like, and laboratory animals such as rats and mice.

An "estrogen-dependent tumor" is a tumor which requires the presence of an estrogenic substance, for example estradiol, for the growth, development and metastatic involvement of the tumor within the subject.

As previously stated, we have discovered that antiestrogenic cyclopropyl analogs can be employed as anti-estrogenic agents, fertility agents, or as anti-tumor agents to substantially prevent the genesis of estrogen dependent tumors, and to inhibit the growth, development, and metastatic involvement of existing estrogen-dependent tumors in a subject. The anti-estrogenic cyclopropyl analogs which can be administered to a subject as an anti-estrogenic, anti-tumor or fertility agent in accordance with the present invention are represented by the generic structure (Structure I)

wherein:

X is a halogen or hydrogen atom;

$R_1$ is a hydrogen atom, an alkyl group containing from 1 to about 3 carbon atoms, a monocyclic group, a hydroxy substituted monocyclic group, an alkoxy substituted monocyclic group in which the alkyl substituent contains from 1 to about 3 carbon atoms, or an acetoxy substituted monocyclic group;

$R_2$ is a hydrogen atom, an acetate group, a hydroxyl group, an alkoxy group wherein the alkyl substituent contains from 1 to about 3 carbon atoms, a beta-dialkylaminoethoxy group in which the alkyl substituent contains from 1 to about 6 carbon atoms, a beta-monoaminohetero-cycloethoxy group, or pharmaceutically acceptable salts thereof;

$R_3$ is a hydrogen atom, an acetate group, a hydroxyl group, or an alkoxy group in which the alkyl substituent contains from 1 to about 3 carbon atoms;

$R_4$ is a hydrogen atom, or an alkyl group containing from 1 to about 3 carbon atoms; and the wavy lines ($\sim$) in the structure indicate that the anti-tumor agent can be of the cis-or transisomer.

Any suitable anti-estrogenic cyclopropyl analog meeting the above definition can be employed as the anti-estrogenic agent, fertility agent or anti-tumor agent in the treatment of a subject to prevent the genesis or to inhibit the growth and metastatic involvement of an existing estrogen-dependent tumor in the subject. In one particularly preferred embodiment, the group $R_2$ is different from the group $R_3$. Illustrative of cyclopropyl analogs satisfying the above-defined generic structure and which can be employed as anti-estrogenic agents, fertility agents, or as anti-tumor agents in accordance with the present invention are as follows:

1,1-dichloro-cis-2,3-diphenylcyclopropane
cis-1,2-diphenylcyclopropane
1,1-dichloro-trans-2-methyl-2,3-(4,4'-dimethoxyphenyl) cyclopropane
1,1-dichloro-trans-2,3-dimethyl-2,3-(4,4'-dimethoxyphenyl)cyclopropane
1,1-dichloro-trans-2-methyl-2,3-diphenylcyclopropane
1,1-dichloro-trans-2,3-dimethyl-2,3-diphenylcyclopropane
1,1-dichloro-cis-2-methyl-2,3-diphenylcyclopropane
1,1-dichloro-cis-2,3-dimethyl-2,3-diphenylcyclopropane
cis-1-methyl-1,2-diphenylcyclopropane
1,1-dichloro-cis-2,3-diethyl-2,3-diphenylcyclopropane
1,1-dibromo-cis-2,3-diethyl-2,3-diphenylcyclopropane
1,1-difluoro-cis-2,3-diethyl-2,3-diphenylcyclopropane
1,1-dichloro-(Z)-2-{p-[2-(N,N-dimethylamino)ethoxy]-phenyl}-3-phenylcyclopropane
1,1-dichloro-(Z)-2,3-Bis-{p-[2-(N,N-dimethylamino)ethoxy]phenyl}cyclopropane 1,1-dichloro-(Z)-2-{p-[2-(N,N-diethylamino)ethoxy]-phenyl}-3-phenylcyclopropane 1,1-dichloro-(Z)-2,3-Bis-{p-[2-(N,N-diethylamino)ethoxy]phenyl} cyclopropane 1,1-dichloro-(Z)-2-[p-(2-N-pyrrolidinoethoxy)phenyl]-3-phenylcyclopropane 1,1-dichloro-(Z)-2,3-Bis-[p-(2-N-pyrrolidinoethoxy)phenyl]cyclopropane 1,1-dichloro-3-ethyl-2,2,3-triphenylcyclopropane 1,1-dibromo-3-ethyl-2,2,3-triphenylcyclopropane 1,1-difluoro-3-ethyl-2,2,3-triphenylcyclopropane 1,1-dichloro-cis-2-(p-hydroxyphenyl)-2,3-diphenylcyclopropane 1,1-difluoro-cis-2-(p-hydroxyphenyl)-2,3-diphenylcyclopropane 1,1-dibromo-cis-2-(p-hydroxyphenyl)-2,3-diphenylcyclopropane 1,1-dichloro-2,2-(4,4'dihydroxyphenyl)-3-phenylcyclopropane 1,1-difluoro-2,2-(4,4'dihydroxyphenyl)-3-phenylcyclopropane 1,1-dibromo-2,2-(4,4'dihydroxyphenyl)-3-phenylcyclopropane 1,1-dichloro-(Z)-2-{p-[2-(N,N-dimethylamino)ethoxy]-phenyl}-3-ethyl-2,3-diphenylcyclopropane 1,1-dibromo-(Z)-2-{p-[2-(N,N-dimethylamino)ethoxy]-phenyl}-3-ethyl-2,3-diphenylcyclopropane 1,1-difluoro-(Z)-2-{p-[2-(N,N-dimethylamino)ethoxy]-phenyl}-3-ethyl-2,3-diphenylcyclopropane 1,1-dichloro-(E)-2-{p-[2-(N,N-dimethylamino)ethoxy]-phenyl}-3-ethyl-2,3-diphenylcyclopropane 1,1-dibromo-(E)-2-{p-[2-(N,N-dimethylamino)ethoxy]-phenyl}-3-ethyl-2,3-diphenylcyclopropane 1,1-difluoro-(E)-2{p-[2-(N,N-dimethylamino)ethoxy]-phenyl}-3-ethyl-2,3-diphenylcyclopropane 1,1-dichloro-(Z)-2-{p-[2-(N,N-diethylamino)ethoxy]-phenyl}-3-ethyl-2,3-diphenylcyclopropane 1,1-dibromo-(Z)-2-{p-[2-(N,N-diethylamino)ethoxy]-pheny}-3-ethyl-2,3-diphenylcyclopropane 1,1-difluoro-(Z)-2-{p-[2-(N,N-diethylamino)ethoxy]-phenyl}-3-ethyl-2,3-diphenylcyclopropane 1,1-dichloro-(E)-2-{p-[2-(N,N-diethylamino)ethoxy]-phenyl}-3-ethyl-2,3-diphenylcyclopropane 1,1-dibromo-(E)-2-{p-[2-(N,N-diethylamino)ethoxy]-phenyl}-3-ethyl-2,3-diphenylcyclopropane 1,1-difluoro-(E)-2-{p-[2-(N,N-diethylamino)ethoxy]-phenyl}-3-ethyl-2,3-diphenylcyclopropane 1,1-dichloro-(E)-2-(p-methoxyphenyl)-2{p-[2-(N,N-dimethylamino)ethoxy]phenyl}-3-ethyl-3-phenylcyclopropane 1,1-dichloro-(Z)-2-(p-methoxyphenyl)-2-{p-[2-(N,N-dimethylamino)ethoxy]pheny}-3-ethyl-3-phenylcyclopropane 1,1-dichloro-(E)-2-(p-methoxyphenyl)-2-{p-[2-(N,N-diethylamino)ethoxy]phenyl}-3-ethyl-3-phenylcyclopropane 1,1-dichloro-(Z)-2-(p-methoxyphenyl)-2-{p-[2-(N,N-diethylamino)ethoxy]phenyl}-3-ethyl-3-phenylcyclopropane 1,1-dichloro-(E)-2-(p-methoxyphenyl)-2-[p(2-N-pyrrolidinoethoxy)phenyl]-3-ethyl-3-phenylcyclopropane 1,1-dichloro-(Z)-(p-methoxyphenyl)-2-[p-(2-N-pyrrolidinoethoxy)phenyl]-3-ethyl-3-phenylcyclopropane 1,1-dichloro-(E)-2-(p-hydroxyphenyl)-2-{p-[2-(N,N-dimethylamino)ethoxy]phenyl}-3-ethyl-3-phenylcyclopropane 1,1-dichloro-(E)-2-{p-[2-(N,N-dimethylamino)ethoxy]-phenyl}-2-phenyl-3-(p-methoxyphenyl)-3-ethylcyclopropane 1,1-dichloro-(E)-2-(p-hydroxphenyl)-2-{p-[2-(N,N-dimethylamino)ethoxy]phenyl}-3-(p-methoxyphenyl)-3-ethylcyclopropane 1,1-dichloro-(E)-2-(p-methoxyphenyl)-2{-[p-2-(N-pyrrolidino)ethoxy]phenyl}-3-(p-methoxyphenyl)-3-ethylcyclopropane 1,1-dichloro-trans-2-[(4-methoxy)phenyl]-3-phenylcyclopropane 1,1-dichloro-trans-2[(4-acetoxy)phenyl]-3-phenylcyclopropane 1,1-dichloro-trans-2[(4-hydroxy)phenyl]-3-phenylcyclopropane 1,1-dichloro-2,2-Bis-[(4-methoxy)phenyl]-3-phenylcyclopropane 1,1-dichloro-2,2-Bis-[(4-acetoxy)phenyl]-3-phenylcyclopropane 1,1-dichloro-2,2-Bis-[(4-hydroxy)phenyl]-3-phenylcyclopropane Reduced Cyclopropyl Analogs (Z)-1-{p-[2-(N,N-dimethylamino)ethoxy]pheny}-2-phenylcyclopropane (Z)-1,2-Bis-{p-[2-(N,N-dimethylamino)ethoxy]phenyl} cyclopropane (Z)-1-{p-[2-(N,N-diethylamino)ethoxy]phenyl}-2-phenylcyclopropane (Z)-1,2-Bis-{p-[2-(N,N-diethylamino)ethoxy]phenyl} cyclopropane (Z)-1-[p-(2-N-pyrrolidinoethoxy)phenyl]-2-phenylcyclopropane (Z)-1,2-Bis-[p-(2-N-pyrrolidinoethoxy)phenyl]cyclopropane (E)-1-{p-[2-(N,N-dimethylamino)ethoxy]phenyl}-2-ethyl-1,2-diphenylcyclopropane (E)-1-{p-[2-(N,N-diethylamino)ethoxy]phenyl}-2-ethyl-1,2-diphenylcyclopropane (E)-1-[p-(2N-pyrrolidinoethoxy)phenyl]-2-ethyl-b 1,2-diphenylcyclopropane (Z)-1-{p-[2-(N,N-dimethylamino)ethoxy]phenyl}-2-ethyl-1,2-diphenylcyclopropane (Z)-1-{p-[2-(N,N-diethylamino)ethoxy]phenyl}-2-ethyl-1,2-diphenylcyclopropane (Z)-1-[p-(2N-pyrrolidinoethoxy)phenyl]-2-ethyl-1,2diphenylcyclopropane Pharmaceutically Acceptable Salts of Cyclopropyl Analogs 1,1-dichloro-(Z)-2-{p-[2-(N,N-dimethylamino)ethoxy]-phenyl}-3-phenylcyclopropane hydrochloride (Z)-1-{p-[2-N,N-dimethylamino)ethoxy]phenyl}-2-phenylcyclopropane methanesulfonate 1,1-dichloro-(Z)-2-{p-(2-)N,N-diethylamino)ethoxy]-phenyl}-3-phenylcyclopropane hydrochloride (Z)-1-{p-[2-(N,N-diethylamino)ethoxy]phenyl}-2-phenylcyclopropane hydrochloride 1,1-dichloro-(Z)-2-[p-(2-N-pyrrolidinoethoxy)phenyl]-3-phenylcyclopropane methanesulfonate (Z)-1,2-Bis-[p-(2-N-pyrrolidinoethoxy)phenyl]cyclopropane dihydrochloride

1,1-dichloro-(E)-2-{p-[2-(N,N-dimethylamino)ethoxy]-phenyl}-3-ethyl-2,3-diphenylcyclopropane hydrochloride 1,1-dichloro-(E)-2-{p-[2(N,N-diethylamino)ethoxy]-phenyl}-3-ethyl-2,3-diphenylcyclopropane citrate 1,1-dichloro-(E)-2-[p-(2-N-pyrrolidinoethoxy)phenyl]-3-ethyl-2,3-diphenylcyclopropane methanesulfonate
(E)-1-{p-[2-(N,N-dimethylamino)ethoxy]phenyl}-2-ethyl-1,2-diphenylcyclopropane hydrochloride
(E)-1-{p-[2-(N,N-diethylamino)ethoxy]phenyl}-2-ethyl-1,2-diphenylcyclopropane sulfate
(E)-1-[p-(2-N-pyrrolidinoethoxy)phenyl]-2-ethyl-b 1,2-diphenylcyclopropane methanesulfonat
1,1-dichloro-(Z)-2-[p-(2-N-pyrrolidinoethoxy)phenyl]-3-ethyl-2,3-diphenylcyclopropane methanesulfonate
(Z)-1-{p-[2-(N,N-dimethylamino)ethoxy]phenyl}-2-ethyl-1,2-diphenylcyclopropane hydrochloride
(Z)-1-{p-[2-(N,N-diethylamino)ethoxy]phenyl}-1,2-ethyl-1,2-diphenylcyclopropane sulfate
(Z)-1-[p-(2N-pyrrolidinoethoxy)phenyl]-2-ethyl-1,2-diphenylcyclopropane methanesulfonate
1,1-dichloro-(Z)-2-{p-[2-(N,N-dimethylamino)ethoxy]phenyl}-3-ethyl-2,3-diphenylcyclopropane hydrochloride
1,1-dichloro-(Z)-2-{p-[2-(N,N-diethylamino)ethoxy]phenyl}-3-ethyl-2,3-diphenylcyclopropane citrate
(Z)-1-[p-(2N-pyrrolidinoethoxy)phenyl]-2-ethyl-1,2-diphenylcyclopropane methanesulfonate
1,1-dichloro-(Z)-2-{p-[2-(N,N-dimethylamino)ethoxy]phenyl}-3-ethyl-2,3-diphenylcyclopropane hydrochloride
1,1-dichloro-(Z)-2-{p-(N,N-diethylamino)ethoxy]phenyl}-3-ethyl-2,3-diphenylcyclopropane citrate As previously stated, the cyclopropyl analogs useful as anti-estrogenic agents, fertility agents and as anti-tumor agents in the prevention or treatment of existing estrogen-dependent tumors in a subject can be of either the cis- or trans-isomer. However, initial studies have indicated that cis-isomers of the cyclopropyl analogs are more anti-estrogenic and more effective than the trans-isomers of such cyclopropyl analogs in inducing anti-estrogenic activity, female fertility and in the treatment of a subject to prevent the development and/or retard the growth and metastatic involvement of existing estrogen-dependent tumors in the subject.

The cis-isomer of the anti-estrogenic cyclopropy analogs useful in the practice of the present invention can be represented by the general structure (Structure II)

wherein:
X is a halogen or hydrogen atom;
$R_1$ is a hydrogen atom, an alkyl group containing from 1 to about 3 carbon atoms, a monocyclic group, a hydroxy substituted monocyclic group, an alkoxy substituted monocyclic group in which the alkyl substituent contains from 1 to about 3 carbon atoms, or an acetoxy substituted monocyclic group;
$R_2$ is a hydrogen atom, an acetate group, a hydroxyl group, an alkoxy group in which the alkyl substituent contains from 1 to about 3 carbon atoms, a beta-dialkylaminoethoxy group in which the alkyl substituent contains from 1 to about 6 carbon atoms, a beta-monoaminoheterocycloethoxy group, or pharmaceutically acceptable salts thereof;
$R_3$ is a hydrogen atom, an acetate group, a hydroxyl group, or an alkoxy group in which the alkyl substituent contains from 1 to about 3 carbon atoms; and
$R_4$ is a hydrogen atom, or an alkyl group containing from 1 to about 3 carbon atoms.

While any of the before-defined moieties X, $R_1$, $R_2$, $R_3$, and $R_4$, as well as the different combinations of such moieties, can be utilized to form the cyclopropyl analog anti-estrogenic, fertility and anti-tumor agents of the present invention (and such applies equally to the cis- and trans-isomers of the cyclopropyl analogs as defined by Structure I, as well as the cis-isomers of such analogs defined by Structure II) it is believed that the most desirable effects may be obtained when the respective moieties of the cyclopropyl analogs are a follows:
X is a chlorine, fluorine or bromine atom;
$R_1$ is a hydrogen atom, a phenyl group, a p-hydroxyphenyl group, or a p-methoxyphenyl group;
$R_2$ is a hydrogen atom, a beta-dimethylaminoethoxy group, a beta-diethylaminoethoxy group, a beta-pyrrolidinoethoxy group, or pharmaceutically acceptable salts thereof;
$R_3$ is a hydrogen atom, a hydroxyl group, or a methoxy group; and
$R_4$ is a hydrogen atom or an ethyl group.

Typical compounds falling within the above-defined cyclopropyl analogs which are believed to be especially suitable for use as anti-estrogenic agents or anti-tumor agents in the treatment of estrogen-dependent tumors, or as fertility agents in the treatment of an infertile female subject, are set forth as follows:
1,1-dichloro-cis-2,3-diphenylcyclopropane
1,1-dibromo-cis-2,3-diethyl-2,3-diphenylcyclopropane
1,1-difluoro-cis-2,3-diethyl-2,3-diphenylcyclopropane
1,1-dichloro-3-ethyl-2,2,3-triphenylcyclopropane
1,1-difluoro-3-ethyl-2,2,3-triphenylcyclopropane
1,1-dichloro-cis-2-(p-hydroxyhenyl)-2,3-diphenylcyclopropane
1,1-difluoro-cis-2-(p-hydroxyphenyl)-2,3-diphenylcyclopropane
1,1-dichloro-(Z)-2-{p-[2-(N,N-dimethylamino)ethoxy]phenyl}-3-ethyl-2,3-diphenylcyclopropane
1,1-dichloro-(E)-2-{p-[2-(N,N-dimethylamino)ethoxy]phenyl}-3-ethyl-2,3-diphenylcyclopropane
1,1-dichloro-(Z)-2-{p-[2-(N,N-diethylamino)ethoxy]phenyl}-3-ethyl-2,3-diphenylcyclopropane
1,1-dichloro-(E)-2-{p-[2-(N,N-diethylamino)ethoxy]phenyl)-3-ethyl-2,3-diphenylcyclopropane
1,1-dichloro-(E)-2-(p-methoxyphenyl)-2-{p-[2-(N,Ndimethylamino)ethoxy]phenyl}[-3-ethyl-3-phenylcyclopropane
1,1-dichloro-(Z)-2-(p-methoxyphenyl)-2-{p-[2-(N,Ndiethylamino)ethoxy]phenyl}-3-ethyl-3-phenylcyclopropane
1,1-dichloro-(E)-2-(p-methoxyphenyl)-2-[p-(2-N-pyrrolidinoethoxy)phenyl]-3-ethyl-3-phenylcyclopropane
1,1-dichloro-(Z)-2-(p-methoxyphenyl)-2-[p-(2-N-pyrrolidinoethoxy)phenyl]-3-ethyl-3-phenylcyclopropane
1,1-dichloro-cis-2-[(4-methoxy)phenyl]-3-phenylcyclopropane
1,1-dichloro-cis-2-[(4-acetoxy)phenyl]-3-phenylcyclopropane 1,1-dichloro-cis-2-[(4-hydroxy)phenyl]-3-phenylcyclopropane 1,1-dichloro-cis-2,3-Bis-[(4-methoxy)phenyl]cyclopropane Pharmaceutically Acceptable Salts of Cyclopropyl Analogs 1,1-dichloro-(E)-2-{-[2-(N,N-dimethylamino)ethoxy]-phenyl}-3-ethyl-2,3-diphenylcyclopropane hydrochloride 1,1-dichloro-(E)-2-{p-[2-(N,N-diethylamino)ethoxy]-phenyl}-3-ethyl-2,3-diphenylcyclopropane citrate

1,1-dichloro-(E)-2-[p-(2-N-pyrrolidinoethoxy)phenyl]-3-ethyl-2,3-diphenylcyclopropane methanesulfonate 1,1-dichloro-(Z)-2-{p-[2(N,N-dimethylamino)ethoxy]-phenyl}-3-ethyl-2,3-diphenylcyclopropane hydrochloride 1,1-dichloro-(Z)-2-{p-[2-(N,N-diethylamino)ethoxy]-phenyl}-3-ethyl-2,3-diphenylcyclopropane citrate 1,1-dichloro-(Z)-2-[p-(2-N-pyrrolidinoethoxy)phenyl]-3-ethyl-2,3-diphenylcyclopropane methanesulfonate Other anti-estrogenic cyclopropyl analogs which can be administered to a subject as an anti-estrogenic, anti-tumor or fertility agent in accordance with the present invention are represented by the generic structure (Structure III)

wherein:

X is a halogen or hydrogen atom;

$R_1$ is a hydrogen atom, an acetate group, a hydroxyl group, an alkoxy group wherein the alkyl substituent contains from 1 to about 3 carbon atoms, a beta-dialkylaminoethoxy group in which the alkyl substituent contains from 1 to about 6 carbon atoms, a beta-monoaminoheterocycloethoxy group, or pharmaceutically acceptable salts thereof;

$R_2$ is a hydrogen atom, an acetate group, a hydroxyl group, an alkoxy group wherein the alkyl substituent contains from 1 to about 3 carbon atoms, a beta-dialkylaminoethoxy group in which the alkyl substituent contains from 1 to about 6 carbon atoms, a beta-monoaminoheterocycloethoxy group, or pharmaceutically acceptable salts thereof; and $R_3$ is an alkyl group containing between about 5 and about 9 carbon atoms.

Any suitable anti-estrogenic cyclopropyl analog meeting the above definition can be employed as the anti-estrogenic agent, fertility agent or anti-tumor agent in the treatment of a subject to prevent the genesis or to inhibit the growth and metastatic involvement of a existing estrogen-dependent tumor in the subject. Illustrative of cyclopropyl analogs satisfying the above-defined generic structure and which can be employed as antiestrogenic agents, fertility agents, or as anti-tumor agents in accordance with the present invention are as follows:

1,1-dichloro-2,2-Bis-[(4-methoxy) phenyl]-spiro [2.5]octane 1,1-dichloro-2,2-Bis-[(4-acetoxy) phenyl]-spiro [2.5]octane 1,1-dichloro-2,2-Bis-[(4-hydroxy) phenyl]-spiro [2.5]octane Other anti-estrogenic cyclopropyl analogs which can be administered to a subject as an anti-estrogenic, anti-tumor or fertility agent in accordance with the present invention are represented by the generic structure (Structure IV)

wherein:

X is a halogen or hydrogen atom;

$R_1$ is a hydrogen atom, an alkyl group containing from 1 to about 3 carbon atoms, a monocyclic group, a hydroxy substituted monocyclic group, an alkoxy substituted monocyclic group in which the alkyl substituent contains from 1 to about 3 carbons atoms, or an acetoxy substituted monocyclic group;

$R_2$ is a hydrogen atom, an acetate group, a hydroxyl group, an alkoxy group wherein the alkyl substituent contains from 1 to about 3 carbon atoms, a beta-dialkylaminoethoxy group in which the alkyl substituent contains from 1 to about 6 carbon atoms, a beta-monoaminoheterocycloethoxy group, or pharmaceutically acceptable salts thereof;

$R_3$ is a hydrogen atom or an alkyl group containing from 1 to about 3 carbon atoms;

$R_4$ is a hydrogen atom, or an alkyl group containing from 1 to about 3 carbon atoms; and the wavy lines (∿) in the structure indicate that the anti-tumor agent can be of the cis- or trans-isomer.

Any suitable anti-estrogenic cyclopropyl analog meeting the above definition can be employed as the anti-estrogenic agent, fertility agent or anti-tumor agent in the treatment of a subject to prevent the genesis or to inhibit the growth and metastatic involvement of an existing estrogen-dependent tumor in the subject. Illustrative of cyclopropyl analogs satisfying the above-defined generic structure and which can be employed as anti-estrogenic agents, fertility agents, or as anti-tumor agents in accordance with the present invention are as follows:

1,1-dichloro-2,2-Bis-[(4-methoxy) phenyl]cyclopropane 1,1-dichloro-2-[(4-methoxy) phenyl]-2-[(4-hydroxy) phenyl]cyclopropane 1,1-dichloro-2,2-Bis-[(4-hydroxy) phenyl]cyclopropane The preceding list of the compounds believed especially suitable as anti-tumor agents, anti-estrogenic agents or fertility agents is for illustrative purposes and is not to be construed as limiting the scope of the anti-estrogenic cyclopropyl analogs defined by the above general structures I, II, III and IV.

The dosage of the cyclopropyl analogs defined hereinabove by Structures I, II, III and IV required to induce antiestrogenic activity or to substantially prevent or retard the growth, development and metastatic involvement of an estrogen dependent tumor in a subject can vary widely and will be dependent, to a large degree, upon the weight of the subject, the severity and number of the estrogen-dependent tumors in the subject, if any, and the anti-estrogenic properties of the particular cyclopropyl analog employed as the anti-tumor or antiestrogenic agent. However, it is believed that desirable results can be obtained when the anti-estrogenic cyclopropyl analogs used as the anti-estrogenic agents or anti-tumor agents are administered to the subject in a dosage of from about 0.5 milligrams to about 2 milligrams per kilogram of weight of the subject, and an effective dosage of the cyclopropyl analog agents will generally be about 1 milligram per kilogram of weight of the subject.

The cyclopropyl analogs employed as the anti-estrogenic agents or anti-tumor agents in accordance with the present invention are generally solid materials. Thus, it may be desirable to suspend, emulsify, solubilize, or disperse the anti-estrogenic cyclopropyl analog in a suitable vehicle to facilitate the administration of the anti-tumor agent to the subject. In such instance, any suitable vehicle can be employed provided the vehicle is inert to the anti-estrogenic cyclopropyl analog and to the subject. Such vehicles and the methods for suspending, emulsifying, solubilizing, or dispersing the antiestrogenic cyclopropyl analogs in a suitable vehicle are well known in the art of pharmaceutical formulations and thus a further description of same is not believed necessary herein.

The method of administration of the anti-estrogenic and anti-tumor agents of the present invention (i.e., the anti-estrogenic cyclopropyl analogs) to the subject can be by any suitable means known in the art. For example, the anti-estrogenic or anti-tumor agent can be administered to the subject orally, by implantation, or by the parenteral route of administration which may include intravenous, intramuscular, subcutaneous, intraarterial, and direct tumor perfusion techniques. As previously indicated, we believe that any suitable cyclopropyl analog fulfilling the definition set forth hereinbefore by the Structures I, II, III and IV can be employed as an anti-estrogenic agent or as an anti-tumor agent to prevent or substantially retard the growth, development and metastatic involvement of an estrogen dependent tumor in a subject.

The anti-estrogenic cyclopropyl analogs represented by the Structures I, II, III and IV also exhibit properties which indicate that such anti-estrogenic cylopropyl analogs may be useful as fertility agents in the treatment of an infertile female subject. When employing the anti-estrogenic cyclopropy analogs as fertility agents the dosage of the fertility agent, which may be required to induce the fertility of the infertile female subject, can vary widely and will be dependent, to a large degree upon the weight of the subject, the route of administration employed in the application of the anti-estrogenic cyclopropyl analog and the particular analog employed. However, it is believed that the dosage of the anti-estrogenic cyclopropyl analog fertility agent necessary to stimulate fertility in an infertile subject would be in an amount of from about 0.5 milligrams to about 2 milligrams per kilogram of weight of the subject, and an effective dosage of the anti-estrogenic cyclopropyl analog fertility agent would generally be about 1 milligram per kilogram of weight of the subject.

The anti-estrogenic cyclopropyl analogs which may be employed as fertility agents in accordance with the present invention are generally solid materials. Thus it may be desirable to suspend, emulsify, solubilize, or disperse the anti-estrogenic cyclopropyl analog in a suitable vehicle to facilitate the administration of the fertility agent to the subject. In such instance, any suitable vehicle can be employed provided the vehicle is inert to the analog and to the subject. Such vehicles and the methods for suspending, emulsifying, solubilizing, or dispersing the analogs in the vehicle are well known in the art of pharmaceutical formulations and thus a further description of same is not believed necessary herein.

The method of administration of the anti-estrogenic cyclopropyl analogs for use as a fertility agent to enhance fertility in an infertile female subject can be by any suitable means known in the art. For example, the fertility agent may be administered to the subject orally, by implantation, or by the parenteral route of administration which may include intravenous, intramuscular, subcutaneous, and intra-arterial techniques.

In order to determine the effectiveness of the antiestrogenic cyclopropyl analogs represented by Structures I and II in the treatment f estrogen-dependent tumors, an animal model was employed. The animal model, a DMBA-induced rat mammary tumor model, simulates in many respects the estrogen-dependent tumors in human subjects. Thus, rats having DMBA-induced estrogen-dependent mammary tumors were used to evaluate the effectiveness of the above-defined anti-estrogenic cyclopropyl analogs as anti-tumor agents for estrogen-dependent tumors.

The following examples are given to illustrate the effectiveness of the before-defined anti-estrogenic cyclopropyl analogs in substantially preventing or arresting the growth, development and metastatic involvement of estrogen-dependent tumors. The examples are for illustrative purposes only and are not to be construed as unduly limiting the scope of the invention as hereinafter recited in the claims. All parts and percentages in the examples, unless otherwise specified, are parts by weight and weight percentages.

EXAMPLE I

A series of cyclopropyl analogs were prepared using several procedures. The gem-dichlorocyclopropyl analogs were prepared by either procedure A or B. The reduced analogs (i.e., the analogs without gem-dichlorocyclopropyl groups) were prepared using either the Procedure A or B in combination with Procedure C. It should be noted, however, that in those instances where it was desired that the analog contain a hydroxyl moiety on the phenyl ring, such as in the para position, Procedure A was followed.

In each of the following Procedures A and B, 1,1-dichloro-cis-2,3-diphenylcyclopropane was prepared as an illustrative example of the cyclopropyl analogs for use in the practice of the present invention. When the gem-dichlorocyclopropanes so prepared were reduced to remove the chlorine atoms, such reductions were carried out using sodium metal in wet methanol. Procedure C is illustrative of the before-mentioned reductive procedure in which cis-1,2-diphenylcyclopropane was prepared.

Procedure A—Preparation of gem-dichlorocyclopropyl analogs.

3.6 g (0.02 mole) of cis-stilbene was added to 10.0 g (0.002 mole) of phenyl(bromodichloromethyl)mercury in benzene. After the resulting solution was refluxed with stirring under dry nitrogen and maintained at 82°–88° C. in an oil bath for 1.5 hour with stirring, phenylmercuric bromide precipitated (7.2 g, 92%) and the reaction mixture turned yellow. The relative proton absorption in the NMR spectrum showed small quantities of the unchanged olefin.

The mixture then was refluxed with stirring for an additional hour. The NMR spectrum of this mixture indicated that the olefin had reacted. Benzene was removed on a flash evaporator, yielding 6.5 g of crude product, which was dissolved in petroleum ether (bp 30°–60° C.) and filtered to remove a small amount of white precipitate, mp 175° C. The crude product was purified through a 2×18 cm column of neutral alumina (activity I) using purified petroleum ether (bp 30°–60° C.). A cream-colored oil was eluted, which solidified after standing in a refrigerator overnight. The solid had a melting point range of 49°–51° C. and weighed 4.5 g (86%).

An analytical sample was obtained by sublimation. The sublimator was kept in 45° C. (0.03 mm) in an oil bath while the inner cold finger was maintained at −5° C. by cold water pump. The white needles melted at 50°–51.5° C. NMR and infrared spectra verified the product of 1,1-dichloro-cis-2,3-diphenylcyclopropane.

Procedure B—Preparation of gem-dichlorocyclopropyl analogs.

To a cold solution of 0.50 g (0.002 mole) of triethylbenzylammonium chloride and 110 ml of chloroform in a three-necked flask was added 6.0 g (0.33 mole) of cis-stilbene, and the solution was stirred to dissolve the stilbene. A 50% sodium hydroxide solution (75 g) was added carefully through a dropping funnel; it was stirred a 10°–20° C. for 6 hours and then at room temperature for 24 hours by means of a magnetic stirrer. The mixture was diluted with 100 ml of water, and a dark-brown chloroform layer separated. The aqueous phase was extracted with three 50 ml portions of methylene chloride, and the organic layers were collected and dried over anhydrous magnesium sulfate. Evaporation of the solvent in vacuo yielded 7.5 g of dark-brown oil.

The crude oil was purified by placing it on a 1.3×33 cm column of alumina (activity I) and eluting with purified petroleum ether (bp 30°–60° C.). A cream-colored oil, 6.0 g (69%), solidified at 0° C., and had a mp 48°–49° C.

The IR and NMR spectra of the product were identical to those of the product obtained using Procedure A.

Procedure C—Reduction of gem-dichlorocyclopropyl analogs to remove the chloro groups.

A solution of 2.0 g (0.008 mole) of 1,1-dichloro-cis-2,3-diphenyl-cyclopropane and 30 ml of ether in a 250 ml three-necked flask, fitted with a dry ice-acetone condenser, was stirred (magnetic stirrer) in an ice water bath. Sodium metal (6.9 g; 0.3 g-atom) was added in small pieces over 1.5 hour, and 60 ml of wet methanol (2 ml of water) was introduced slowly through a dropping funnel with stirring (magnetic stirrer). After all of the sodium metal reacted, 20 ml of water was added and the aqueous layer was extracted with two 30 ml portions of ether.

The aqueous phase was neutralized slowly with concentrated hydrochloric acid on an ice-salt bath and extracted with two 30 ml portions of ether. The ether extracts were dried over anhydrous magnesium sulfate and filtered. Evaporation of ether at 30° C. under vacuum yielded 1.5 g of yellow oil, which solidified when left at 0° C. Sublimation at 40°–50° C. (0.04–0.05 mm) with the cold finger at −40° C. yielded 1.0 g (68%) of white needles, mp 38°–38.5° C. NMR and Infrared spectra verified the production of cis-1,2-diphenylcyclopropane. The cylopropyl analogs so prepared and utilized in the following test procedures are tabulated as follows:

TABLE I

| Analog No. | CYCLOPROPYL ANALOGS Chemical Name |
|---|---|
| I | 1,1-Dichloro-trans-2,3-diphenylcyclopropane |
| II | 1,1-Dichloro-cis-2,3-diphenylcyclopropane |
| III | Trans-1,2-Diethyl-1,2-(4,4'-dimethoxyphenyl)-cyclopropane |
| IV | 1,1-Dichloro-trans-2,3-diethyl-2,3-(4,4'-dihydroxyphenyl)cyclopropane |
| V | 1,1-Dichloro-trans-2,3-diethyl-2,3-(4,4'-diacetoxyphenyl)cyclopropane |
| VI | 1,1-Dichloro-trans-2,3-(4,4'-dimethoxyphenyl)-cyclopropane |
| VII | 1,1-Dichloro-trans-2,3-diethyl-2,3-(4,4'-dimethoxyphenyl)cyclopropane |
| VIII | Trans-1,2-Diethyl-1,2-(4,4,-dihydroxyphenyl)-cyclopropane |
| IX | Cis-1,2-Diphenylcyclopropane |
| X | Trans-1,2-Diphenylcyclopropane |

EXAMPLE II

Procedure D—Preparation of 1,1-dichloro-cis-2-(p-methoxyphenyl)-3-phenylcyclopropane, 1,1-dichloro-cis-2-(p-hydroxyphenyl)-3-phenylcyclopropane and 1,1-dichloro-cis-2-(p-acetoxyphenyl)-3-phenylcyclopropane.

A mixture of 27.23 g (0.20 mole) of 4-methoxy benzaldehyde and 27.23 g (0.20 mole) of phenyl acetic acid was added to a mixture of 20 ml of triethylamine and 40 ml of acetic anhydride. This solution was refluxed with stirring over 4–5 hours. The reaction mixture was cooled and 200 ml of 20% sodium hydroxide was added. Anhydrous diethyl ether was used to extract this mixture and the combined ethereal layers were discarded. The aqueous layer was acidified with concentrated hydrochloric acid resulting in a solid which was removed by filtration. Purification of the product was accomplished by recrystallization from aqueous ethanol which yielded 27.0 g (54%) of cis-α-phenyl-p-methoxy cinnamic acid in the form of light yellow needles.

A solution of 12.70 g (0.05 mole) of cis-α-phenyl-p-methoxy cinnamic acid in 64.5 g (0.50 mole) quinoline was stirred as 0.90 g of copper chromite was added. To achieve decarboxylation, the mixture was heated to 180° C. which releases carbon dioxide. The presence of quinoline prevents isomerization to the more stable trans configuration during the heating stage. The mixture was kept at 180°–190° C. for 1½ hours. The solution was transferred after cooling to a separatory funnel with 100 ml of anhydrous diethyl ether. Approximately 500 ml of 15% hydrochloric acid solution was used to extract the residual quinoline. The ether layer was filtered to remove particles of the catalyst, and washed with saturated sodium chloride solution. That layer was then dried with magnesium sulfate and concentrated by rotary vacuum evaporation. The brown residual oil was purified by vacuum distillation to yield 6.0 g (57%) of cis-methoxy stilbene.

A solution of 5.25 g (25 mMol) of cis-p-methoxy stilbene and 0.57 g (2.5 mMol) of triethylbenzyl ammonium chloride in 80 ml of chloroform was stirred while 60 g of 29% cold sodium hydroxide solution was added by drops. The solution was stirred for 20 hours. Layers were separated and the aqueous layer was extracted with three 50 ml portions of methylene chloride. The combined organic layers were washed with three 50 ml portions of saturated salt solution and dried over anhydrous magnesium sulfate. Filtration and concentration produced a dark brown oil which was heated with 30 ml of petroleum ether, and then was filtered to remove the insoluble residue. After the petroleum ether was evaporated, a small amount of ethanol was added and cooled at 0° C. to give a light brown solid. After recrystallization with ethanol, 1,1-dichloro-cis-2-(p-methoxyphenyl)-3-phenylcyclopropane was formed.

A solution comprising 3.0 ml of dry methylene chloride and 2.1 ml of n-Butanephiol was stirred under argon. To this solution was added 1.33 g (10 mMol) of aluminum chloride. Also added to this solution was 0.586 g (2 mMol) of 1,1-dichloro-cis-2-(p-methoxyphenyl)-3-phenylcyclopropane in 10 ml of dry methylene chloride by drops. The mixture was stirred at room temperature for 40 minutes and then cooled in an ice bath. Ice cold water was added by drops slowly to decompose the aluminum chloride. After the layers were separated, three 10 ml portions of anhydrous diethyl ether were used to extract the aqueous layer. The combined organic layers were dried with magnesium sulfate, filtered and concentrated to yield a brown oil (crude yield 90%). Unreacted n-Butanephiol and a byproduct n-Butyl methyl sulfide were evaporated by connecting the crude product to a vacuum pump which yielded a light brown oil containing 1,1-dichloro-cis2-(p-hydroxyphenyl)-3-phenylcyclopropane.

A solution of 10 ml of anhydrous diethyl ether, 10.0 mMol of crude product of 1,1-dichloro-cis-2-(p-hydroxyphenyl)-3-phenylcyclopropane and 0.79 g (10 mMol) of pyridine was heated to gentle refluxing. Acetyl chloride, 0.78 g (10 mMol), was added by drops very slowly, which immediately formed a white precipitate. The mixture continued to reflux gently for one hour after all the acetyl chloride was added. The reaction flask was cooled in an ice bath while 5.0 ml of water was added by drops. The aqueous layer was extracted by using three 10 ml portions of anhydrous diethyl ether. The combined ether layer was washed with three 10 ml portions of 5% sulfuric acid and saturated sodium bicarbonate solution. It was then dried with sodium sulfate and evaporated to give a dark yellow oil which was purified by column chromatography on silica gel with methylene chloride-petroleum ether (3:1) as eluent to yield a yellow oil containing 1,1-dichloro-cis-2-(p-acetoxyphenyl)-3-phenylcyclopropane.

Procedure E—Preparation of 1,1-dichloro-2,2-Bis-(p-methoxyphenyl) cyclopropane, 1,1-dichloro-2-(p-methoxyphenyl)-2-(p-hydroxyphenyl) cyclopropane and 1,1-dichloro-2,2-Bis-(p-hydroxyphenyl) cyclopropane.

A Grignard reagent was prepared with 2.43 g (0.1 mole) of magnesium turning and 18.7 g (0.1 mole) p-bromoanisole in 20 ml of dry ether. It was refluxed for 30 minutes after mos of the magnesium had dissolved. To this solution was added by drops 3.97 g (45 mMol) of ethyl acetate in 10 ml of dry ether over 30 minutes, and the reaction mixture was refluxed for one hour. The mixture was cooled to room temperature; 40 ml of 5N sulfuric acid and 40 ml of ether was added slowly. The mixture was stirred for a few hours and allowed to sit overnight. The layers were then separated and the aqueous layer was extracted with chloroform and then washed with a saturated salt solution, dried over anhydrous magnesium sulfate, and evaporated to give the alkene product as a light yellow solid. Recrystallization in ethanol yielded 4.0 g (37%) white flaky solid comprising 1,1-Bis-(p-methoxyphenyl) ethylene.

A solution of 4.8 g (20 mMol) of 1,1-Bis-(p-methoxyphenyl) ethylene and 0.46 g (2 mMol) of triethylbenzyl ammonium chloride in 80 ml of chloroform was stirred while 48 g of 29% cold sodium hydroxide solution (166 ml) was added by drops over 2 hours. This was stirred for 17 hours. Layers were separated and the aqueous layer was extracted with three 50 ml portions of methylene chloride. The combined organic layer was washed with three 50 ml portions of saturated salt solution and dried over anhydrous magnesium sulfate. Filtration and concentration yielded a yellow solid which was recrystallized in ethanol to give yellow needles. Further recrystallization with cyclohexane-ethanol (40:50) yielded 4.66 g (72%) yellow needles containing 1,1-dichloro-2,2-Bis-(p-methoxyphenyl) cyclopropane.

Placed in an oven-dried, three-necked flask was 1.615 g (5 mMol) of 1,1-dichloro-2,2-Bis-(p-methoxyphenyl) cyclopropane which was flushed with argon and sealed with a rubber septum. Using oven-dried syringes, 10 ml of chloroform, 0.32 g (4 mMol) of pyridine and 2.9 ml (20 mMol) of iodotrimethylsilane were injected into the flask in the order specified above (the chloroform and pyridine had been dried previously over anhydrous magnesium sulfate). The mixture turned yellow and a white precipitate was noted with the addition of iodotrimethylsilane. The mixture was heated to reflux without stirring for 72 hours. Thin layer chromatography was performed with methylene chloride and a small amount of starting material still was present. Anhydrous methanol, dried with magnesium sulfate, in the amount of 2.5 ml was added and the mixture turned golden brown. It was cooled to room temperature and transferred to a round bottom flask with 10 ml of chloroform. The volatile components were removed on a rotary evaporator to yield a yellow solid which was dissolved in 50 ml of ether. The insoluble pyridium hydrochloride was filtered. The ether was evaporated to afford a yellow solid whose NMR and thin layer chromatography (with methylene chloride-acetone (95:5)) showed starting material along with some polar components. These components were separated by column chromatography on silica gel (125 g) with methylene chloride-acetone (95:5) as eluent. Unreacted starting material was eluted first and 0.4 g was recovered. Compound 1,1-dichloro-2-(p-methoxyphenyl)-2-(p-hydroxyphenyl) cyclopropane was eluted next and recrystallized in hexane with trace of ethanol to give colorless fine needles. The column was then washed with acetone, and compound 1,1-dichloro-2,2-Bis-(p-hydroxyphenyl) cyclopropane as a red brown solid was obtained upon evaporation of the solvent. This solid was recrystallized in chloroform to give a light pink solid.

Procedure F—Preparation of 1,1 dichloro-2,2-Bis-(p-methoxyphenyl)-3-phenylcyclopropane.

A solution of 6.9 g (30 mMol) of p-methoxy deoxybenzoin in 20 ml of benzene was prepared and 6.9 g (33 mMol) of phosphorus pentachloride added thereto. After stirring at room temperature for 15 hours the reaction was completed. This mixture was poured into 50 g of crushed ice and 40 ml of ether was used to rinse out the flask. The layers were separated, and the aqueous layer was extracted with three 40 ml portions of ether. The combined ether layer was dried over anhydrous sodium sulfate. A reddish oil obtained upon evaporation of the solvent solidified immediately. It was washed with methanol and recrystallized in ether to yield 5.1 g (70%) of p-methoxy-α'-chlorostilbene.

A solution was made from 4.8 g (20 mMol) of p-methoxy-α'-chlorostilbene and 2.6 g (24 mMol) of anisole in 12 ml of carbon disulfide. To this solution, 3.4 g (26 mMol) pulverized aluminum chloride was added slowly over 30 minutes. The mixture turned crimson red and was stirred at room temperature for 4 hours. About 40 g of crushed ice and 40 ml of ether was added and the reaction mixture turned to a yellowish color upon decomposition of the aluminum chloride. The layers were separated, and the aqueous layer was extracted with three 20 ml portions of ether. Combined ether layer was washed with two 25 ml portions of saturated salt solution (brine), and dried over anhydrous sodium sulfate. An orange oil obtained was dissolved in hot ethanol and cooled at 0° C. A yellow oil precipitated while the colorless supernatant was piped out carefully. A colorless solid was crystallized from this supernatant. Subsequent treatment of the yellow oil with ethanol yielded 4.55 g (72%) solid 1,1-Bis-(p-methoxyphenyl)-2-phenyl ethylene.

A solution was prepared containing 4.74 g (15 mMol) of 1,1-Bis-(p-methoxyphenyl)-2-phenyl ethylene and 0.34 g (1.5 mMol) of triethylbenzyl ammonium chloride in 45 ml of chloroform. To this solution 34 g of 50% cold sodium hydroxide solution (69 ml) was added by drops through a dropping funnel. The mixture was stirred vigorously at room temperature for 8 hours, and diluted with 40 ml of water. A dark brown chloroform layer was separated, and the aqueous layer was extracted with three 25 ml portions of methylene chloride. The combined organic layer was washed over three 40 ml portions of saturated salt solution (brine), and dried over anhydrous magnesium sulfate. Evaporation of the solvent in vacuo yielded 6.6 g dark brown syrupy oil which was dissolved in hot hexane. Some insoluble brown crust was filtered and the hexane filtrate was cooled at 0° C. to yield a yellow solid which was recrystallized in cyclohexane-ethanol (60:40) to give light yellow crystals comprising 1,1-dichloro-2,2-Bis-(p-methoxyphenyl)-3-phenylcyclopropane.

Procedure G—Preparation of 1,1-dichloro-2,2-Bis-(p-methoxyphenyl)spiro [2.5]octane.

A Grignard reagent was prepared with 1.94 g (80 mMol) of magnesium turning and 15.0 g (80 mMol) of p-bromoanisole in 40 ml of dry ether. Methyl cyclohexane carboxylate, 5.7 g (40 mMol), in 15 ml dry ether was added by drops over 20 minutes. After an hour of refluxing, the reaction mixture was poured into an acidic solution of 30 g of ice, 30 ml of water, and 6.0 ml of concentrated sulfuric acid for hydrolysis. The aqueous layer was then extracted with three 20 ml portions of ether. The combined ether layer was washed with two 50 ml portions of 10% sulfuric acid solution and dried over anhydrous sodium sulfate. Filtration and evaporation yielded an orange yellow oil which is shown to be Bis-(p-methoxyphenyl)-cyclohexyl methanol. The dehydration was accomplished by combining 3.0 ml of concentrated sulfuric acid in 10.0 ml of acetic acid and adding this solution slowly by drops to the Bis-(p-methoxyphenyl)cyclyohexyl methanol while it was cooled in an ice bath. The mixture turned dark red and solidified. A small amount of ether was added to facilitate the stirring. After 2 hours of stirring at room temperature, 20 ml of water and 20 ml of ether were added. The aqueous layer was extracted with three 15 ml portions of ether, and the combined ether layer was washed with two 25 ml portions of saturated salt solution (brine), and dried over anhydrous sodium sulfate. Upon evaporation of the solvent, the yellow solid obtained was recrystallized in ethanol. Further recrystallization affords 8.0 g (65%) colorless solid containing Bis-(p-methoxyphenyl)-cyclo hexylidene methane.

A solution of 6.16 g (20 mMol) of Bis-(p-methoxyphenyl)-cyclohexylidene methane and 0.46 g (2 mMol) of triethylbenzyl ammonium chloride in 65 ml of chloroform was stirred while 48 g of 50% cold sodium hydroxide solution (96 ml) was added by drops. The mixture was stirred vigorously for 84 hours at room temperature. The layers were separated, and the aqueous layer was extracted with five 30 ml portions of methylene chloride. The combined organic layer was washed with five 50 ml portions of saturated salt solution (brine), and dried over anhydrous sodium sulfate. Filtration and evaporation afforded a dark brown thick oil which was dissolved in hot petroleum ether. Some insoluble brown crust was filtered as well as a yellow solid precipitate from the petroleum ether filtrate. Colorless fine needles were obtained from subsequent recrystallizations in cyclohexane containing 1,1-dichloro-2,2-Bis-(p-methoxyphenyl)-spiro [2.5]octane.

Procedure H—Preparation of 1,1-dichloro-cis-2,3-Bis-(p-methoxyphenyl) cyclopropane.

A solution of 5.68 g (20 mMol) of 2,3-Bis-(p-methoxyphenyl) acrylic acid in 10.0 ml of quinoline was stirred while 0.4 g of copper chromite was added. Carbon dioxide was released when the temperature of the reaction mixture reached 180° C. The solution was then cooled and 60 ml of ether was used to transfer the reaction mixture to a separatory funnel. Approximately 500 ml of 15% hydrochloric solution was used to extract the residual quinoline. The ether layer was filtered to remove particles of catalyst, and washed with saturated sodium chloride solution. It was then dried over anhydrous magnesium sulfate and concentrated to yield a dark brown oil. The trans-olefin in the amount of 0.07 g was collected when ethanol was used to attempt crystallization. Petroleum ether was used to dissolve the brown oil and cool at 0° C. to give the cis-isomer as flaky solid. Recrystallization yielded 2.81 g (58%) solid containing Bis-(p-methoxy)-cis-stilbene.

A solution of 6.46 g (27 mMol) of Bis-(p-methoxy)-cis-stilbene and 0.46 g (2.0 mMol) of triethylbenzyl ammonium chloride in 65 ml of chloroform was stirred while 40 g of 29% cold sodium chloride solution (138 ml) was added by drops. The vigorous stirring was continued for 17½ hours. The layers were separated and the aqueous layer was extracted with three 50 ml portions of methylene chloride. The combined organic layer was washed with three 50 ml portions of saturated sodium chloride solution and dried over anhydrous magnesium sulfate. Filtration and concentration yielded a dark brown oil which was heated to dissolve in hexane. After some insoluble brown crust was filtered, the hexane filtrate was allowed to cool to give a yellow solid which was recrystallized in ethanol to yield 5.57 g (64%) light yellow fine needles containing 1,1-dichloro-cis-2,3-Bis-(p-methoxyphenyl) cyclopropane.

EXAMPLE III

Procedure J—Biological Methods—Uterotropic Assay for Estrogenic and Anti-estrogenic Activity—The assay for estrogenic activity employed immature Swiss-Webster mice weighing 10–14 g (approximately 21 days old). The animals were randomly distributed into groups containing 5–6 mice each. Estradiol and the test compounds were dissolved separately in sesame oil and administered subcutaneously in a volume of 0.1 ml. Control animals were treated with the same volume of sesame oil alone.

All animals were treated daily for three consecutive days. On the fourth day the animals were sacrificed and the uteri carefully dissected, blotted lightly and weighed to the nearest 0.1 mg. Body weights were also recorded. Estradiol was used in a dosage range of 0.01–0.04 ug (total dose) as the assay standard. Each cyclopropyl analog was examined over a dosage range of 1–25 ug (total dose).

The uterotropic assay was also used to evaluate the anti-estrogenic activity of the test compounds which did not produce an estrogenic response in the previous assay. The anti-estrogenic assay was conducted as described above for estrogenic activity except that each animal in the cyclopropyl analog treatment groups received a standard stimulating dose of estradiol (0.04 ug). The test compounds and estradiol were administered separately at different injection sites to minimize possible physical interaction or reduced absorption of either compound. Anti-estrogenic activity was measured as a decrease in estradiol-stimulated uterotropic response in groups which received both the test compound and estradiol as compared to a group which was treated with estradiol alone.

A line of best fit was plotted for each compound which produced an estrogenic or anti-estrogenic response. Regression analysis was used to calculate each line. The slope of the response to each analog was compared to the slope of the estradiol response to determine parallelism in this assay system. The relative uterotropic activity of each compound was expressed as a percentage of estradiol activity.

Histological Preparation and Examination—Mouse uterine tissue was fixed in 10% formaldehyde, embedded in paraffin, sectioned on a microtome and stained with hemotoxylin-eosin. Slides were examined with a compound light microscope and various measurements of uterine horn cross sections were made. These measurements, which were made on each cross section at several levels along the uterine horn, included:

(1) total uterine horn diameter or thickness, at two different points;
(2) endometrial thickness at two different points as measured from the endometrial-myometrial border to maximum invagination of the endometrium into the lumen of the uterine horn.

Photomicrographs of uterine horn cross sections and ephithelial linings were taken with a camera attached to a compound light microscope.

Anti-Tumor Assay—In this study 50 day old female Sprague-Dawley rats received a single oral dose of 10 mg of 7,12-dimethylbenz(a)anthracene (DMBA) dissolved in 1 ml of corn oil via stomach tube. The animals were examined and palpated for tumors at weekly intervals until tumors were detected. Animals which displayed tumors of 1–3 cm in their largest diameter were included in the study. The rats were distributed into experimental groups on the basis of total tumor volume and number so that each group contained approximately the same mean tumor volume and mean number at the beginning of the treatment period. Rats in the ovariectomized group had both ovaries removed one day prior to the initiation of the treatment period.

Analog II and tamoxifen were dissolved separately in olive oil at a concentration of 1.2 mg/ml. One treatment group received 0.6 mg of analog II, (0.5 ml, s.c.) three times a week; another treatment group received 0.6 mg of tamoxifen three times a week, at the same concentration; the control group received an equal volume of olive oil at the same frequency. Tumor size was determined twice weekly in all groups using a vernier caliper to measure the major and minor diameter of each tumor. Tumor volume (V) was calculated based on an ellipsoid tumor shape ($V = 4/3 \pi r_1^2 r_2$, where $r_1$ is the minor tumor radius).

Receptor Binding Assay—Uteri were removed from female Sprague-Dawley rats weighing approximately 250 g. The uteri were cleaned of connective tissue and homogenized in 5 vol. (w/v) ice-cold Tris buffer A containing 0.02M Tris (hydroxymethyl) aminomethane hydrochloride, 0.0015M disodium ethylenediamine tetraacetate, 0.25M sucrose and the pH was adjusted to 7.4. The tissue was homogenized using a motor driven ground glass tissue homogenizer placed in an ice-water bath. The homogenate was centrifuged at 100,000 X g for 1 hour at 4° C. using a swinging bucket rotor on an ultracentrifuge.

The supernatant (cytosol) was used immediately after preparation in the receptor binding assay. Incubations were conducted for 20 hours at 4° C. in a total volume of 0.5 ml of Tris buffer A containing 100–150 ul uterine cytosol, 0.025 uCi 2,4,6,7 (n)-[$^3$H] 17B-estradiol (327 mCi/mg) and various concentrations of the test compounds. Each test compound was assayed at 3 concentrations over a range of $10^{-4}$ to $10^{-6}$ molar for the cyclopropyl analogs and $10^{-7}$ to $10^{-9}$ molar for the estradiol standard. The test compounds were dissolved in ethanol and in all cases the final concentration of the ethanol was less than 2% of the incubation media. At the end of the incubation period the cytosol-bound [$^3$H]-estradiol was separated from unbound [$^3$H]-estradiol by the addition of 0.5 ml of a Dextran-coated charcoal solution (Tris buffer A containing 0.05% Dextran-70 and 0.5% Norit A charcoal). The assay tubes were vortexed and centrifuged at 500 X g for 15 minutes. The [$^3$H]-estradiol concentration of a 0.5 ml aliquot of the supernatant was determined by liquid scintillation spectrometry. Counting times were automatically adjusted to obtain a counting error of less than 1% using a liquid scintillation counter. The [$^3$H]-estradiol displacement for each test compound was determined by linear regression analysis and plotted graphically. The relative receptor binding activity of each analog was determined using the ratio: (concentration of unlabeled estradiol producing 70% displacement of [$^3$H]-estradiol/concentration of cyclopropyl analog producing 70% displacement of [$^3$H]-estradiol X 100).

BIOLOGICAL RESULTS

The analogs set forth in Table I were tested to determine their estrogenic and anti-estrogenic activity using the uterotropic assay. The relative estrogenic activity of the analogs was determined to be that the estrogenic activity of analog VIII > analog IV > analog V. These analogs produced between 1.5% and 2.5% of the uterotropic response of estradiol on a molecular weight basis as reported in Table II hereinafter. Cyclopropyl analogs which displayed no estrogenic activity in the uterotropic assay were further tested for anti-estrogenic activity. As shown by the data of Table II, only analog II produced an anti-estrogenic response.

Since the uterotropic response is a nonspecific measure of estrogenic activity, the uteri were examined histologically to confirm the estrogenic nature of the uteropic response. Estradiol and the cyclopropyl analogs (IV and VIII) produced a significant (P<0.001) increase in uterine diameter and endometrial thickness which represent a specific estrogenic response (Table III).

The cyclopropyl analogs were tested for receptor binding activity and compared to the estradiol standard. All of the analogs were capable of displacing [$^3$H]-estradiol from the estrogen receptor. However, analogs IV, VIII and V (in that order) displayed the greatest binding activity which ranged from 4% to 50% of the receptor binding activity produced by estradiol on a molecular weight basis (Table III).

Figure 1:
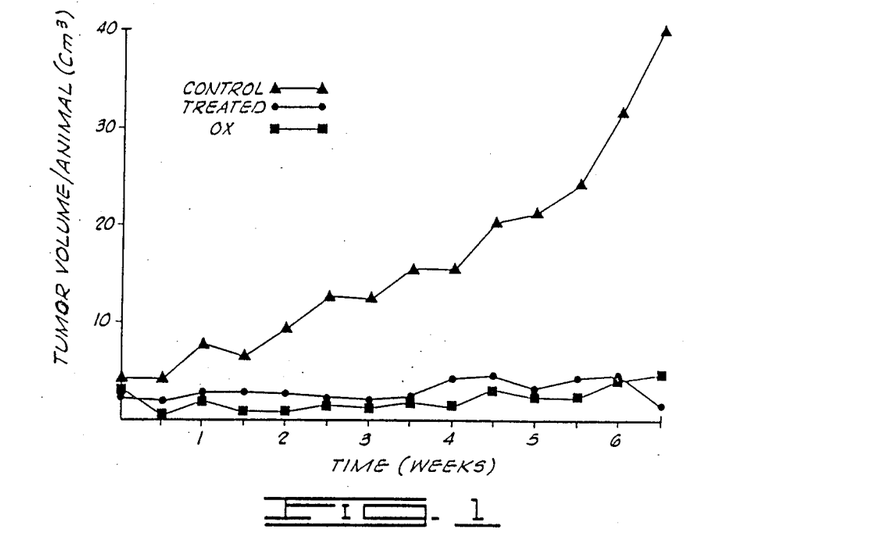
FIG. 1 is a graphic illustration of the influence of an anti-estrogenic cyclopropyl analog (1,1-dichloro-cis-2,3-diphenylcyclopropane) and ovariectomy (OX) on DMBA (7,12-dimethylbenz(a)anthracene)-induced rat mammary tumor volume.
Figure 2:
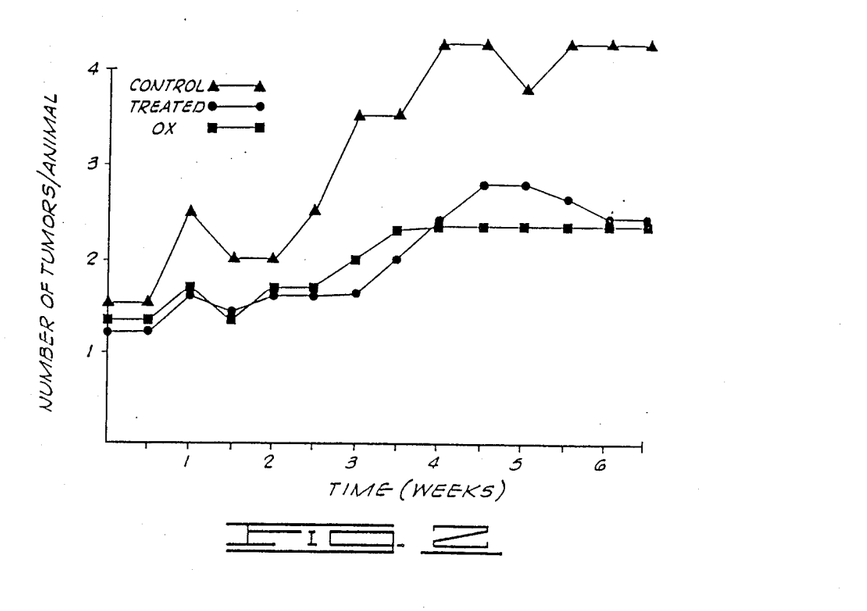
FIG. 2 is a graphic illustration of the influence of an anti-estrogenic cyclopropyl analog (1,1-dichloro-cis-2,3-diphenylcyclopropane) and ovariectomy (OX) on DMBA (7,12- dimethyl- benz(a)anthracene)- induced rat mammary tumor number per animal.

The anti-tumor activity of the anti-estrogen (analog II) was examined using the 7,12-dimethylbenz(a) anthracene-induced mammary tumor assay in the rat in two separate experiments. In the first experiment the tumor data were expressed as both tumor volume/animal (FIG. 1) and tumor number/animal (FIG. 2). Ovariectomy produced a slightly greater reduction in tumor volume during the first 3 weeks of the treatment period while tumor volume in the treated group remained essentially unchanged. Castration is known to cause regression of DMBA-induced tumors and was employed in the present study to verify the estrogen dependent nature of the tumors in the population of rats included in this study. The number of tumors/animal increased in all 3 groups during the treatment period; however, both ovariectomy (OX) and analog II reduced tumor incidence to approximately the same extent when compared to the control group (see FIGS. 1 and 2). The total weight gain during the treatment period in the control and treated groups was not significantly different; thus, suggesting that the anti-tumor activity of analog II was not the result of a general toxic effect of the compound. At the end of the treatment period all animals were sacrificed and the tumors were verified histologically to be adenocarcinomas.

Figure 3:
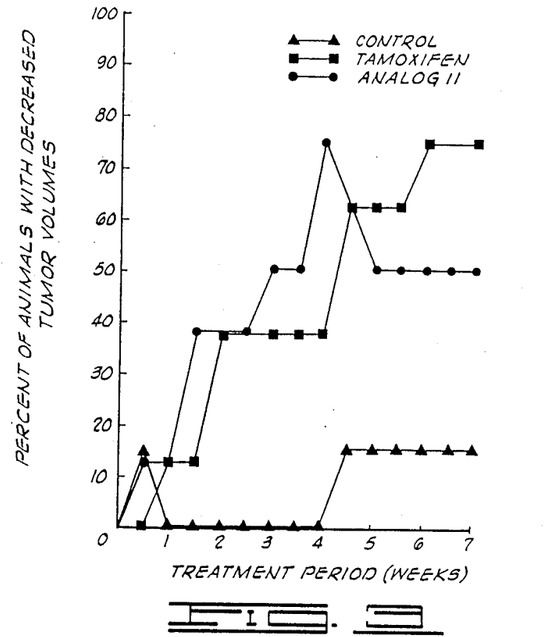
FIG. 3 is a graphic illustration of the influence of an anti-estrogenic cyclopropyl analog (1,1-dichloro-cis-2,3-diphenylcyclopropane) and tamoxifen, Z-1{p-[2-(N,N-dimethylamino)ethoxy]phenyl}-1,2-diphenylbut-1-ene, on the percent of animals with decreased tumor volume.
Figure 4:
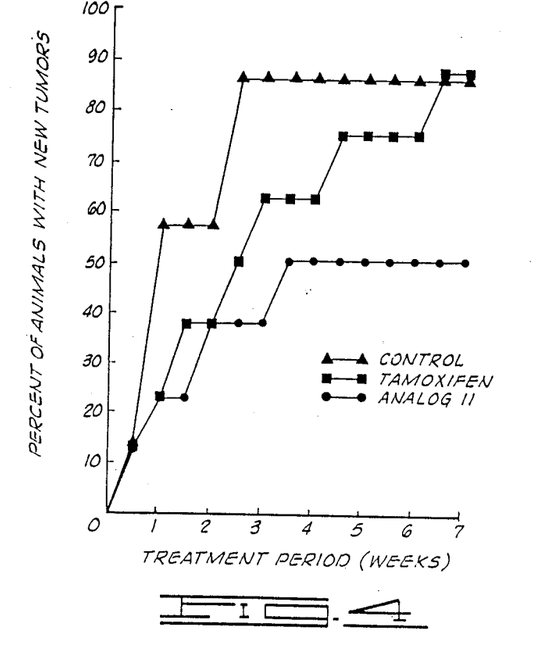
FIG. 4 is a graphic illustration of an anti-estrogenic cyclopropyl analog (1,1-dichloro-cis-2,3-diphenylcyclopropane) and tamoxifen, Z-1{p-[2-(N,N-dimethylamino)ethoxy]phenyl}-1,2-diphenylbut-1-ene, on the percent of animals with new tumors developing during the treatment period.

The second tumor experiment was a parallel study which compared the anti-tumor activity of analog II to tamoxifen, which is a commercially available anti-estrogen which is presently used in the treatment of estrogen-dependent tumors in human subjects. The results of this parallel study are expressed in two ways: (A) percent of animals with decreased tumor volume (FIG. 3); and (B) percent of animals with new tumors developing during the treatment period (FIG. 4). Considering the influence of anti-estrogen treatment on decreased tumor volume (FIG. 3) analog II was found to significantly increase the percent of animals with a decreased tumor volume (P<0.02, FIG. 3) between the 3rd and 5th week of therapy when compared to the control group. Similarly, tamoxifen significantly brought about a higher percentage of animals with a decreased tumor volume between the 5th and 7th week of therapy (P<0.02, FIG. 3). There were no differences between the treatment groups and control groups in the percent of animals with no change in tumor volume. Thus, the overall impression is that analog II and tamoxifen are similar in their ability to reduce the growth of mammary tumors.

FIG. 4 illustrates that at the end of the treatment period 4 of the 8 analog II-treated animals had developed 9 new tumors while 6 of the 7 control rats developed 12 new tumors and 7 of the 8 tamoxifen-treated animals developed 17 new tumors. Thus, analog II protected 50 percent of the animals against new tumor development while only 12 percent of the tamoxifen-treated animals and 14 percent of the control animals were similarly protected.

TABLE II

Estrogenic, Anti-estrogenic and Receptor Binding Activity of the Cyclopropyl Analogs.

| Compound No. | Configuration | X | $R_1$ | $R_4$ | $R_2$ & $R_3$ | Relative Uterotropic Activity[a] | Antiestrogenic Activity[b] | Relative Receptor Binding Activity[c] |
|---|---|---|---|---|---|---|---|---|
| Estradiol | | | | | | 100 | — | 100 |
| Analog I | Trans | Cl | H | H | H | — | — | 0.02 |
| Analog II | Cis | Cl | H | H | H | — | 36 ug | 0.0086 |
| Analog III | Trans | H | $C_2H_5$ | $C_2H_5$ | $OCH_3$ | — | — | 0.4 |
| Analog IV | Trans | Cl | $C_2H_5$ | $C_2H_5$ | OH | 1.63 | — | 48.6 |
| Analog V | Trans | Cl | $C_2H_5$ | $C_2H_5$ | $OCOCH_3$ | 1.57 | — | 3.6 |
| Analog VI | Trans | Cl | H | H | $OCH_3$ | — | — | 0.0038 |
| Analog VII | Trans | Cl | $C_2H_5$ | $C_2H_5$ | $OCH_3$ | — | — | 0.049 |
| Analog VIII | Trans | H | $C_2H_5$ | $C_2H_5$ | OH | 2.55 | — | 9.1 |
| Analog IX | Cis | H | H | H | H | — | — | 0.0045 |
| Analog X | Trans | H | H | H | H | — | — | 0.0064 |

[a] Activity expressed as a percentage of estradiol activity.
[b] Dose of analog which would produce a 50% reduction in the uterotropic response to 0.04 ug estradiol.
[c] Concentration of estradiol that displaced 70% [$^3$H]-estradiol − concentration of analog that displaced 70% [$^3$H]-estradiol × 100.

TABLE III

Histological Examination of Uterine Sections.

| Compound | Dose (ug) | Uterine Diameter (mm) Mean ± SD | Endometrial Thickness (mm) Mean ± SD |
|---|---|---|---|
| Control | — | 0.56 ± 0.15 | 0.16 ± 0.04 |
| Estradiol | 0.04 | 1.42 ± 0.24[a] | 0.49 ± 0.15[a] |

TABLE III-continued

Histological Examination of Uterine Sections.

| Compound | Dose (ug) | Uterine Diameter (mm) Mean ± SD | Endometrial Thickness (mm) Mean ± SD |
|---|---|---|---|
| Analog IV | 5.0 | 1.53 ± 0.19[a] | 0.48 ± 0.12[a] |
| Analog VIII | 5.0 | 1.30 ± 0.15[a] | 0.40 ± 0.07[a] |

[a] Significantly different from control P < 0.001.

Thus, the above data indicates that analog II was more effective than tamoxifen in protecting animals against the development of new tumors during the treatment period.

Each of the cyclopropyl analogs set forth in this Example were found to bind, in a specific manner, to the estrogen receptor; and each of the analogs possessed little or no estrogenic activity relative to estradiol (e.g., less than about 1 percent, on a molar basis, of the estrogenic activity of estradiol). Thus, it is apparent that the anti-estrogenic cyclopropyl analogs as hereinbefore defined have potential as effective therapeutic agents in the treatment of estrogen-dependent tumors and as fertility agents. Further, the biological results relating to the anti-estrogenic properties of analog II (the cis-isomer) were totally unexpected since the trans-isomer of stilbene and stilbenediol derivatives (which contains a double bond) have heretofore been known to possess greater activity than the corresponding cis-isomer. Further the most active established anti-estrogens (i.e., the di- and triarylethylenes) are known to be the trans-isomers.

EXAMPLE IV

A series of cyclopropyl analogs were prepared using the procedures A, B, and C set forth in Example I, and the cyclopropyl analogs so prepared were subjected to a series of experiments to determine the estrogen receptor binding activity of each of the analogs tabulated in Table IV. The estrogen receptor binding activities of the analogs of Table IV are reported in Table V.

TABLE IV

| Analog No. | CYCLOPROPYL ANALOGS Chemical Name |
|---|---|
| XI | 1,1-dichloro-trans-2-methyl-2,3-(4,4'-dimethoxydiphenyl)cyclopropane |
| XII | 1,1-dichloro-trans-2,3-dimethyl-2,3-(4,4'-dimethoxydiphenyl)cyclopropane |
| XIII | 1,1-dichloro-trans-2-methyl-2,3-diphenyl-cyclopropane |
| XIV | 1,1-dichloro-trans-2,3-dimethyl-2,3-diphenylcyclopropane |
| XV | 1,1-dichloro-cis-2-methyl-2,3-diphenyl-cyclopropane |
| XVI | 1,1-dichloro-cis-2,3-dimethyl-2,3-diphenylcyclopropane |
| XVII | 1-methyl-trans-1,2-(4,4'-dimethoxy-diphenyl)cyclopropane |
| XVIII | trans-1,2-dimethyl-1,2-(4,4'-dimethoxy-diphenyl)cyclopropane |
| XIX | trans-1-methyl-1,2-diphenylcyclopropane |
| XX | trans-1,2-Dimethyl-1,2-diphenylcyclopropane |
| XXI | cis-1-methyl-1,2-diphenylcyclopropane |

BIOLOGICAL RESULTS

Each analog as set forth in Table IV was tested initially in the uterotropic assays for estrogenic and antiestrogenic activity as described in Example I. It was determined that none of the analogs listed in Table IV displayed estrogenic or anti-estrogenic activity in the assay system employed.

The cyclopropyl analogs listed in Table IV, were further tested for receptor binding activity as described in Example I. The data tabulated in Table V indicates that all of the analogs listed in Table IV were capable of specific binding to the estrogen receptor.

Each of the anti-estrogenic cyclopropyl analogs set forth in this Example was found to bind, in a specific manner, to the estrogen receptor, and each of the analogs possessed no estrogenic activity. Thus, it is apparent that the anti-estrogenic cyclopropyl analogs as hereinbefore defined have potential as effective therapeutic agents in the treatment of estrogen dependent tumors and as fertility agents. However, analogs IV, V, and VIII exhibited substantially greater estrogen-receptor binding activity and uterotropic activity than the other analogs of Tables I and II (i.e., analogs IV, V and VIII had greater than about 1 percent, on a molar basis of the estrogenic activity of estradiol) and thus would not be suitable as fertility agents. Thus, analogs IV, V and VIII are specifically excluded from the compounds represented by Structure I, which would be suitable as fertility agents in the treatment of infertile female subjects.

TABLE VI

Receptor Binding Activity of the Cyclopropyl Analogs.

| Compound No. | Isomer Configuration | X | R₁ | R₄ | R₂ & R₃ | Relative Binding Activity[a] (% Estradiol Response) |
|---|---|---|---|---|---|---|
| Estradiol | | | | | | 100 |
| XI | trans | Cl | CH₃ | H | O—CH₃ | 8.3 × 10⁻⁵ |
| XII | trans | Cl | CH₃ | CH₃ | O—CH₃ | 5.9 × 10⁻⁴ |
| XIII | trans | Cl | CH₃ | H | H | 5.3 × 10⁻⁴ |
| XIV | trans | Cl | CH₃ | CH₃ | H | 5.1 × 10⁻⁴ |
| XV | cis | Cl | CH₃ | H | H | 6.3 × 10⁻⁴ |

TABLE VI-continued
Receptor Binding Activity of the Cyclopropyl Analogs.

| Compound No. | Isomer Configuration | X | $R_1$ | $R_4$ | $R_2$ & $R_3$ | Relative Binding Activity[a] (% Estradiol Response) |
|---|---|---|---|---|---|---|
| XVI | cis | Cl | $CH_3$ | $CH_3$ | H | $5.5 \times 10^{-4}$ |
| XVII | trans | H | $CH_3$ | H | $O-CH_3$ | $7.3 \times 10^{-4}$ |
| XVIII | trans | H | $CH_3$ | $CH_3$ | $O-CH_3$ | $2.2 \times 10^{-3}$ |
| XIX | trans | H | $CH_3$ | H | H | $1.5 \times 10^{-4}$ |
| XX | trans | H | $CH_3$ | $CH_3$ | H | $1.1 \times 10^{-4}$ |
| XXI | cis | H | $CH_3$ | H | H | $8.0 \times 10^{-4}$ |

[a] $\dfrac{\text{Concentration of estradiol that displaced 50\% [}^3\text{H]-estradiol}}{\text{Concentration of analog that displaced 50\% [}^3\text{H]} - \text{esteradiol}} \times 100$

EXAMPLE V

The compounds 1-1-dichloro-cis-2,3-diphenylcyclopropane (analog II) and 1-1-dibromo-trans-2,3-diphenylcyclopropane (analog XXII) were tested to determine their estrogenic and anti-estrogenic activity using the uterotropic assay.

The assay for estrogenic activity employed immature Sprague-Dawley rats approximately 21 days old, weighing 40–50 g. The animals were randomly distributed into groups containing three rats each. The test compounds were dissolved separately in corn oil and administered subcutaneously in a volume of 0.1 ml. Control animals were treated with the same volume of corn oil alone.

All animals were treated daily for three consecutive days. Animals receiving the test compounds received a total dose of 100 ug of test compound. On the fourth day, the animals were sacrificed and the uteri carefully dissected, blotted lightly and weighed to the nearest 0.1 mg. Body weights were also recorded. The relative estrogenic activity of the test compounds was expressed in terms of the percentage change in uterine weight in treated animals as compared to uterine weight in control animals.

The uterotropic assay was also used to evaluate the anti-estrogenic activity of the test compounds. The anti-estrogenic assay was conducted as described above for estrogenic activity, except that each animal treated with test compounds also received a standard stimulating dose of estradiol, 0.2 ug total dose over three days.

TABLE VI
Estrogenic and Anti-estrogenic Activity of Cyclopropyl Analogs

| Compound No. | Configuration | X | $R_1$ | $R_4$ | $R_2$ & $R_3$ | Estrogenic Assay % change in control uterine weight | Antiestrogenic Assay % change in estrogen stimulated uterine weight |
|---|---|---|---|---|---|---|---|
| Analog II | cis | Cl | H | H | H | −29.5% | −38.5% |
| Analog XXII | trans | Br | H | H | H | −0.4% | −25.1% |

The test compounds and estradiol were administered separately at different injection sites in order to minimize possible physical inter-action or reduced absorption of other compounds. Control animals received only the standard stimulating dose of estradiol. The anti-estrogenic activity of the test compounds was expressed as a percentage change in estrogen-stimulated uterine weight as compared to the uterine weight of an estrogen-stimulated control animal.

The results of these tests are shown in Table VI. The results reveal that analog XXII displays anti-estrogenic activity, although not to the extent of that displayed by analog II. Further, the results reveal both analog II and analog XXII do not display estrogenic activity, in contrast to many other anti-estrogens now in clinical use. Thus, it is believed that analog XXII is suitable for use as an anti-tumor, fertility and anti-estrogen agent in accordance with the present invention.

It is clear that the present invention is well adapted to carry out the objects and attain the ends and advantages mentioned, as well as those inherent therein. While a presently preferred embodiment has been described for purposes of this disclosure, numerous changes may be made which will readily suggest themselves to those skilled in the art and which are encompassed within the spirit of the invention disclosed and as defined in the appended claims.

What is claimed is:

1. A method for inducing anti-estrogenic activity in a mammal in need of such activity comprising administering to the mammal an anti-estrogenically effective, non-toxic dosage of the compound having the structure wherein:
X is chlorine;
$R_1$ is a hydrogen atom;
$R_2$ is a hydrogen atom;
$R_3$ is a hydrogen atom;
$R_4$ is a hydrogen atom; and
the compound is characterized by a cis structure.

2. A method for preventing the development of estrogen-dependent tumors in a subject in need of such therapy or to substantially arrest the growth and metastatic involvement of existing estrogen-dependent tumors in a subject in need of such therapy, the method comprising administering to the subject a therapeutically effective, non-toxic dosage of the compound having the structure wherein:
X is chlorine;
$R_1$ is a hydrogen atom;
$R_2$ is a hydrogen atom;
$R_3$ is a hydrogen atom;
$R_4$ is a hydrogen atom; and
the compound is characterized by a cis structure.

* * * * *